(12) United States Patent
Ogawa et al.

(10) Patent No.: US 8,853,462 B2
(45) Date of Patent: Oct. 7, 2014

(54) METHOD FOR PRODUCING HEXAFLUOROACETONE OR HYDRATE THEREOF

(75) Inventors: Yuta Ogawa, Ibaraki (JP); Yusuke Takahashi, Ibaraki (JP); Akira Endo, Ibaraki (JP); Sunao Ikeda, Ibaraki (JP)

(73) Assignee: Unimatec Co., Ltd., Tokyo (JP)

( * ) Notice: Subject to any disclaimer, the term of this patent is extended or adjusted under 35 U.S.C. 154(b) by 0 days.

(21) Appl. No.: 14/124,085

(22) PCT Filed: May 10, 2012

(86) PCT No.: PCT/JP2012/062021
§ 371 (c)(1),
(2), (4) Date: Dec. 5, 2013

(87) PCT Pub. No.: WO2012/172893
PCT Pub. Date: Dec. 20, 2012

(65) Prior Publication Data
US 2014/0121416 A1    May 1, 2014

(30) Foreign Application Priority Data
Jun. 17, 2011 (JP) .................................. 2011-134747

(51) Int. Cl.
*C07C 45/59* (2006.01)
*C07C 45/40* (2006.01)
*C07C 29/00* (2006.01)

(52) U.S. Cl.
CPC ................. *C07C 45/59* (2013.01); *C07C 45/40* (2013.01); *C07C 29/00* (2013.01)
USPC ............ 568/386; 568/404; 568/405; 568/407

(58) Field of Classification Search
USPC .................................. 568/386, 404, 405, 407
See application file for complete search history.

(56) References Cited

U.S. PATENT DOCUMENTS

| | | | |
|---|---|---|---|
| 3,321,515 A | 5/1967 | Moore et al. | |
| 4,337,361 A | 6/1982 | Anello et al. | |

FOREIGN PATENT DOCUMENTS

| | | |
|---|---|---|
| JP | 40-27173 | 11/1940 |
| JP | 44-13923 B1 | 6/1969 |
| JP | 52-083436 | 7/1977 |
| JP | 57-081433 | 5/1982 |
| JP | 59-157045 | 9/1984 |
| JP | 64-026527 | 1/1989 |
| JP | 02-250864 | 10/1990 |
| JP | 07-233094 | 9/1995 |
| JP | 2001-081056 | 3/2001 |
| JP | 2003-313175 | 11/2003 |

OTHER PUBLICATIONS

International Preliminary Report on Patentability and Written Opinion based on corresponding PCT application No. PCT/JP2012/062021 dated Jan. 3, 2014 (6 pgs).

*Primary Examiner* — Sikarl Witherspoon
(74) *Attorney, Agent, or Firm* — Brinks Gilson & Lione

(57) ABSTRACT

Hexafluoroacetone or a hydrate thereof is produced with a high yield by subjecting a 1-fluoro-4,4-bis(trifluoromethyl)-2,3,5-trioxolanyl ether compound represented by the general formula:

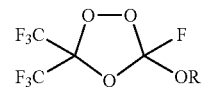

wherein R is an alkyl group having 1 to 8 carbon atoms, an aryl group, or a benzyl group, which has been obtained by ozone oxidation of a heptafluoroisobutenyl ether compound, to a reduction reaction in the presence of a reducing agent selected from dialkyl sulfide containing an alkyl group having 3 or 4 carbon atoms, diaryl sulfide, diaryl disulfide, and diaralkyl sulfide.

6 Claims, No Drawings

METHOD FOR PRODUCING HEXAFLUOROACETONE OR HYDRATE THEREOF

RELATED APPLICATION

This application is a 35 U.S.C. §371 national phase filing of International Patent Application No. PCT/JP2012/062021, filed May 10, 2012, through which and to which priority is claimed under 35 U.S.C. §119 to Japanese Patent Application No. 2011-134747, filed Jun. 17, 2011.

TECHNICAL FIELD

The present invention relates to a method for producing hexafluoroacetone or a hydrate thereof. More particularly, the present invention relates to a method for producing hexafluoroacetone or a hydrate thereof with a high yield by subjecting an ozonide compound, which has been obtained by ozone oxidation of a heptafluoroisobutenyl ether compound, to a reduction reaction in the presence of an organic sulfide compound reducing agent.

Hexafluoroacetone is used, for example, as a monomer for the production of synthetic resin, synthetic rubber, etc.; an intermediate for crosslinking agents, such as bisphenol AF; or an intermediate material for medicines, agrochemicals, etc.

BACKGROUND ART

It is conventionally proposed producing hexafluoroacetone hydrates with such various applications by the following methods:

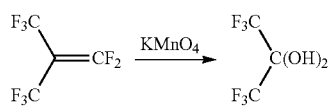

(1)

(Non-Patent Document 1)

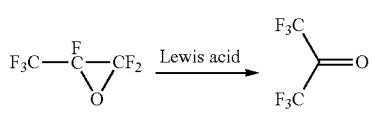

(2)

(Patent Document 1)

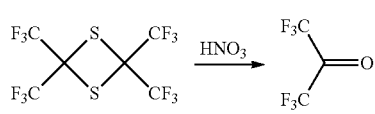

(3)

(Patent Document 2)

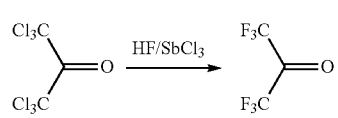

(4)

(Patent Document 3)

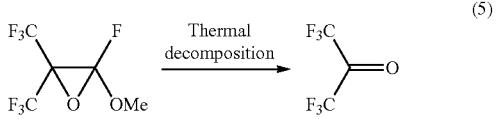

(5)

(Patent Document 4)

However, these methods each have defects, such as production of a large amount of industrial waste, low purity of the product, high toxicity of the reagent used, and corrosion of the reactor. None of these methods is thus economically or environmentally advantageous.

The present applicant has previously proposed a method for producing hexafluoroacetone or a hydrate thereof via an intermediate ozonide compound:

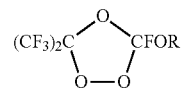

produced by subjecting heptafluoroisobutenyl alkyl, aryl, or benzyl ether $(CF_3)_2C=CFOR$ to ozone oxidation (Patent Document 5).

Reaction examples of subjecting a carbon-carbon double bond chain to ozone oxidation to produce an ozonide intermediate, and subjecting the ozonide intermediate to a reduction reaction to convert it into a carbonyl group are known. Some of such examples are shown below:

Patent Document 6 describes the production of a prostaglandin synthetic intermediate, wherein the butenyl group of a synthetic starting material is subjected to ozone oxidation, followed by a reduction reaction in the presence of triphenylphosphine (Examples 30 and 32).

Patent Document 7 describes the production of a steroid derivative, wherein a carbon-carbon double bond is subjected to ozone oxidation, and the obtained ozonide is subjected to a reduction reaction in the presence of dimethyl sulfide (Reference Example 1).

Patent Document 8 describes subjecting a 4-alkyl-5-alkenylthiazole compound to ozone degradation, and subjecting the obtained ozonide compound to a reduction reaction in the presence of a reducing agent, such as lower alkyl disulfides, aryl phosphines, alkyl phosphines, alkyl phosphites, aryl phosphites, alkali metal bisulfites, alkali metal metabisulfites, alkali metal sulfites, alkali metal dithionites, thiodi-lower alkyl alcohols, thiodi-lower alkyl carboxylic acids, thiodialkylnitriles, thiodiphenols, or thiocarbamides.

Here, dimethyl sulfide, diethyl sulfide, dipropyl sulfide, etc., are shown as examples of lower alkyl disulfides. Dimethyl sulfide is used in Example 14 of Patent Document 8. When this ozonide compound reducing agent is used (Example 14), the target 4-methyl-5-formylthiazole is obtained with the highest yield, as compared to when other ozonide compound reducing agents are used. Diethyl sulfide and dipropyl sulfide are considered to also have the same effect as that of dimethyl sulfide.

PRIOR ART DOCUMENT

Patent Document

Patent Document 1: U.S. Pat. No. 3,321,515
Patent Document 2: U.S. Pat. No. 4,337,361

Patent Document 3: JP-B-40-27173
Patent Document 4: JP-A-2001-81056
Patent Document 5: JP-A-64-26527
Patent Document 6: JP-B-59-46937
Patent Document 7: JP-A-2-250864
Patent Document 8: JP-A-2003-313175
Patent Document 9: JP-A-7-233094
Patent Document 10: JP-A-57-81433
Patent Document 11: JP-A-59-157045

Non-Patent Document

Non-Patent Document 1: Can. J. Chem., vol. 33, page 453 (1955)

OUTLINE OF THE INVENTION

Problem to be Solved by the Invention

An object of the present invention is to provide a method for producing hexafluoroacetone or a hydrate thereof with a high yield by subjecting an ozonide compound, which has been obtained by ozone oxidation of a heptafluoroisobutenyl ether compound, to a reduction reaction in the presence of an organic sulfide compound reducing agent.

Means for Solving the Problem

The above object of the present invention can be achieved by a method for producing hexafluoroacetone or a hydrate thereof, the method comprising subjecting a 1-fluoro-4,4-bis(trifluoromethyl)-2,3,5-trioxolanyl ether compound represented by the general formula:

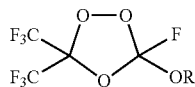

wherein R is an alkyl group having 1 to 8 carbon atoms, an aryl group, or a benzyl group, to a reduction reaction in the presence of a reducing agent selected from dialkyl sulfide containing an alkyl group having 3 or 4 carbon atoms, diaryl sulfide, diaryl disulfide and diaralkyl sulfide.

Effect of the Invention

A 1-fluoro-4,4-bis(trifluoromethyl)-2,3,5-trioxolanyl ether compound can be easily obtained by subjecting a heptafluoroisobutenyl ether compound to ozone oxidation. A method of subjecting this compound to a reduction reaction using a specific ozonide reducing agent can produce, with a high yield, hexafluoroacetone or a hydrate thereof that is useful as an intermediate for crosslinking agents, such as bisphenol AF, or an intermediate starting material for medicines, agrochemicals, etc., and that is found to be applicable to various usages.

Patent Document 8, mentioned above, refers to lower alkyl disulfides, such as dimethyl sulfide, diethyl sulfide, and dipropyl sulfide, as examples of ozonide compound reducing agents. In Example 14, which used a dimethyl sulfide reducing agent, the target product was obtained with the highest yield, as compared to when other ozonide compound reducing agents were used, as described above; however, in the present invention, which differs in a reduction reaction product, the yield of hexafluoroacetone trihydrate is not always good when dimethyl sulfide is used as an ozonide compound reducing agent (Comparative Example 1, described later). In contrast, the yield of hexafluoroacetone trihydrate at a level of 90% is improved by 3 to 5% when dipropyl sulfide or dibutyl sulfide is used as an ozonide compound reducing agent. Further, when diphenyl sulfide or diphenyl disulfide is used, the yield is improved by 5 to 7%.

EMBODIMENTS FOR CARRYING OUT THE INVENTION

The 1-fluoro-4,4-bis(trifluoromethyl)-2,3,5-trioxolanyl ether compound, which is used as a starting material in the method of the present invention, is produced by subjecting a heptafluoroisobutenyl ether compound represented by the general formula $(CF_3)_2C=CF(OR)$ to ozone oxidation.

The heptafluoroisobutenyl ether compound used in ozone oxidation can be easily obtained by subjecting octafluoroisobutene $(CF_3)_2C=CF_2$, which is produced as a by-product in the production of hexafluoropropene, to an addition reaction with a $C_2$-$C_6$ alcohol compound, an aryl compound (e.g., phenol), or an aralkyl compound (e.g., benzyl alcohol); and removing hydrogen fluoride from the addition reaction product $(CF_3)_2CHCF_2OR$ using a hydroxide or carbonate of alkali metal or alkaline earth metal or a base (e.g. trialkylamine), such as potassium hydroxide, in the presence of a phase-transfer catalyst, such as a quaternary ammonium salt (see Patent Document 4).

The ozone oxidation of the heptafluoroisobutenyl ether compound is performed by charging starting materials in a glass reactor, etc., and bringing them into contact with ozone-containing oxygen gas or air while stirring at a temperature of about −70 to 100° C., preferably about −40 to 60° C., in the absence or presence of a solvent, such as hydrocarbon, halogenated hydrocarbon, ether, or water. The ozone concentration of the oxygen gas or air is generally, but not limited to, about 0.1 to 1,000 mg/L, preferably about 1 to 500 mg/L, and the molar ratio of ozone to the starting materials is about 1.

The structure of the 1-fluoro-4,4-bis(trifluoromethyl)-2,3,5-trioxolanyl ether compound, which is a reaction product of ozone oxidation, can be confirmed by the following means.

(a) Characteristic absorption at a wavelength of 1,230 cm$^{-1}$ derived from an oxirane ring in the infrared absorption spectrum (b) Bonding pattern of fluorine atoms determined by $^{19}$F-NMR (c) Bonding pattern of hydrogen atoms determined by $^1$H-NMR (d) Strong characteristic peaks derived from a mass spectrum (M/Z) of 228

The 1,2,4-trioxolane ring of the obtained 1-fluoro-4,4-bis(trifluoromethyl)-2,3,5-trioxolanyl ether compound has very high activity, and is easily cleaved in the presence of a reduction catalyst to form hexafluoroacetone and methyl fluoroformate.

The reduction reaction of the 1-fluoro-4,4-bis(trifluoromethyl)-2,3,5-trioxolanyl ether compound to hexafluoroacetone is performed by charging starting materials in a glass reactor, etc., and reacting them with a specific ozonide reducing agent in the presence or absence of a solvent in a nitrogen atmosphere at a temperature of about −60 to 30° C., preferably −40° C. to 20° C. When a reaction solvent is used, the type of solvent is not particularly limited as long as it is inert to oxolane compounds and ozonide reducing agents; however, fluorine-based solvents, such as 1,1,1,3,3-pentafluorobutane (mfc365), are generally used.

Any of known ozonide reducing agents can be used as long as they can reductively decompose ozonide (see Patent Document 9). Examples thereof include sulfide compounds (dimethyl sulfide and dialkyl disulfide are exemplified); sulfur-containing compounds, such as sodium thiosulfate; phosphorus-containing compounds, such as triethyl phosphite, triphenyl phosphine, and phosphite; metal or metal compounds, such as zinc, Raney nickel, and sodium borohydride; and the like. In the present invention, dialkyl sulfide containing an alkyl group having 3 or 4 carbon atoms (i.e., dipropyl sulfide or dibutyl sulfide), diaryl sulfide typified by diphenyl sulfide, diaryl disulfide typified by diphenyl disulfide, or diaralkyl sulfide typified by dibenzyl sulfide is used. For example, diphenyl disulfide having a melting point of 62° C. is used as an organic solvent solution, such as toluene.

The proportion of such a sulfide compound is about 1 to 10 mol per 1 mol of the 1-fluoro-4,4-bis(trifluoromethyl)-2,3,5-trioxolanyl ether compound.

After completion of the reaction, the produced gas is generally guided sequentially to a water trap, an ice-cold trap, and a dry ice/methanol trap to collect a product. Hexafluoroacetone is obtained as a hydrate aqueous solution mainly in the water trap and the ice-cold trap.

The production of hexafluoroacetone in the gas produced by the reaction can be confirmed by GLC analysis. However, the produced gas contains other by-product gases; thus, hexafluoroacetone is not directly separated, but a method of guiding the decomposed gas into water to form a hydrate, and separating or analyzing the hydrate is used as a simple and useful method.

The obtained hexafluoroacetone hydrate itself can be used as a solvent for polyester, polyamide, or the like; however, the hexafluoroacetone hydrate can be dehydrated by using phosphorus pentoxide, concentrated sulfuric acid, sulfur trioxide, or a molecular sieve (see Patent Documents 10 and 11).

EXAMPLES

The following describes the present invention with reference to Examples.

Reference Example 100 g (0.43 mol) of heptafluoroisobutenyl methyl ether (purity: 91%) was charged in a 500-ml three-necked flask, and brine at −20° C. was passed through a Dimroth condenser. While stirring at 0° C., about 165 L (ozone dose: about 0.43 mol) of oxygen gas containing ozone at a concentration of about 125 mg/L was bubbled for 5 and a half hours.

After completion of the reaction, 115.0 g of crude product (purity: 63.3%) was taken and distilled under reduced pressure, thereby obtaining 51.3 g (yield: 45.0%) of 1-fluoro-4,4-bis(trifluoromethyl)-2,3,5-trioxolanyl methyl ether (purity: 98%) as a fraction of 41 to 43° C./1.4 to 1.7 kPa.

Infrared absorption spectrum: 1230 cm$^{-1}$ (2,3,5-trioxolane)

$^{19}$F-NMR (TFA, CH$_2$Cl$_2$): −15.3 ppm (d, j=2.19 Hz, 1F)
+0.58 ppm (dq, j=2.19, 2.63 Hz, 3F)
+1.90 ppm (q, j=2.63 Hz, 3F)
$^1$H-NMR (TMS, CDCl$_3$): 3.58 ppm (s, 3H)
Mass spectrum (EI, M/Z): 260 (M$^+$)

Comparative Example 1

100 g (0.38 mol) of 1-fluoro-4,4-bis(trifluoromethyl)-2,3,5-trioxolanyl methyl ether (purity: 98%) was charged in a 500-ml five-necked flask. While performing nitrogen bubbling, brine at −20° C. was passed through a Dimroth condenser. While stirring at a reaction temperature of −20° C., 23.4 g (0.38 mol) of dimethyl sulfide was added dropwise using a dropping funnel over 30 minutes. The gas obtained by the reaction was collected by a water trap cooled with ice water to 0° C., and the obtained aqueous layer was analyzed by $^{19}$F-NMR. As a result, it was confirmed that 73.8 g (yield: 89%) of hexafluoroacetone trihydrate was obtained.

Comparative Example 2

In Comparative Example 1, 150 ml of glacial acetic acid was added dropwise over 10 minutes, in place of dimethyl sulfide. Then, while maintaining the system at about 30° C., 49.0 g (0.75 mol) of zinc slab was added in small batches and stirred for 1 hour. As a result, it was confirmed that 68.0 g (yield: 82%) of hexafluoroacetone trihydrate was obtained.

Comparative Example 3

In Comparative Example 1, 188 g (1.131 mol) of triethyl phosphite was added over 15 minutes, in place of dimethyl sulfide. Then, the mixture was stirred overnight. As a result, it was confirmed that 75.5 g (yield: 91%) of hexafluoroacetone trihydrate was obtained.

Example 1

In Comparative Example 1, 44.9 g of dipropyl sulfide in the same molar amount (0.38 mol) was added dropwise in place of dimethyl sulfide at a reaction temperature of 20° C. to perform the reaction, thereby obtaining 78.7 g (yield: 95%) of hexafluoroacetone trihydrate.

Example 2

In Comparative Example 1, 55.6 g of dibutyl sulfide in the same molar amount (0.38 mol) was added dropwise in place of dimethyl sulfide at a reaction temperature of 15° C. to perform the reaction, thereby obtaining 77.1 g (yield: 93%) of hexafluoroacetone trihydrate.

Comparative Example 4

In Comparative Example 1, 76.9 g of dihexyl sulfide in the same molar amount (0.38 mol) was added dropwise in place of dimethyl sulfide at a reaction temperature of 30° C. to perform the reaction, thereby obtaining 74.6 g (yield: 90%) of hexafluoroacetone trihydrate.

Example 3

In Comparative Example 1, 70.7 g of diphenyl sulfide in the same molar amount (0.38 mol) was added dropwise in place of dimethyl sulfide at a reaction temperature of 30° C. to perform the reaction, thereby obtaining 80.4 g (yield: 97%) of hexafluoroacetone trihydrate.

Example 4

In Comparative Example 1, 82.9 g of diphenyl disulfide (used as a solution dissolved in 110.5 g of toluene) in the same molar amount (0.38 mol) was added dropwise in place of dimethyl sulfide at a reaction temperature of 30° C. to perform the reaction, thereby obtaining 78.7 g (yield: 95%) of hexafluoroacetone trihydrate.

The invention claimed is:

1. A method for producing hexafluoroacetone or a hydrate thereof, the method comprising subjecting a 1-fluoro-4,4-bis(trifluoromethyl)-2,3,5-trioxolanyl ether compound represented by the general formula:

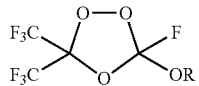

wherein R is an alkyl group having 1 to 8 carbon atoms, an aryl group, or a benzyl group, to a reduction reaction in the presence of an ozonide reducing agent selected from dipropyl sulfide, dibutyl sulfide, and diphenyl disulfide.

2. The method for producing hexafluoroacetone or a hydrate thereof according to claim 1, wherein an ozonide reducing agent is used in an amount of 1 to 10 mol per 1 mol of the 1-fluoro-4,4-bis(trifluoromethyl)-2,3,5-trioxolanyl ether compound.

3. The method for producing a hexafluoroacetone hydrate according to claim 1, wherein the produced hexafluoroacetone is collected by a water trap to form a hexafluoroacetone hydrate aqueous solution.

4. The method for producing hexafluoroacetone according to claim 1, wherein after the hexafluoroacetone is formed into a hydrate aqueous solution, the solution is hydrated.

5. The method for producing hexafluoroacetone according to claim 2, wherein after the hexafluoroacetone is formed into a hydrate aqueous solution, the solution is hydrated.

6. The method for producing hexafluoroacetone according to claim 3, wherein after the hexafluoroacetone is formed into a hydrate aqueous solution, the solution is hydrated.

* * * * *